United States Patent [19]

Hakim et al.

[11] 4,261,341

[45] Apr. 14, 1981

[54] METHOD AND APPARATUS FOR THE TREATMENT OF ASCITES

[75] Inventors: Salomón Hakim, Bogota, Colombia; Carlos A. Hakim, Fort Lauderdale, Fla.

[73] Assignee: Hakim Company Limited, Saint Vincent, British Virgin Isls.

[21] Appl. No.: 46,947

[22] Filed: Jun. 8, 1979

[51] Int. Cl.³ .............................................. A61B 19/00
[52] U.S. Cl. ............................... 128/1 R; 128/350 V; 3/1
[58] Field of Search ............... 128/1 R, 350, 214, 273, 128/274; 3/1 R

[56] References Cited

U.S. PATENT DOCUMENTS

| | | | |
|---|---|---|---|
| 3,496,878 | 2/1970 | Hargest et al. | 3/1 |
| 3,527,226 | 9/1970 | Hakim | 128/350 V |
| 3,669,094 | 6/1972 | Heyer | 128/350 V |
| 3,910,283 | 10/1975 | Leveen | 128/350 V |

OTHER PUBLICATIONS

"LeVeen Shunts" *The Lancet*, Mar. 4, 1978, p. 505 by Arnot et al.
"Hepatorenal Syndrome" *VII International Congress of Nephrology*, Kinney et al. Jun. 1978, Abstracts.
"The LeVeen Peritoneo-Veneus Shunt" Becton-Dickinson Co. (Advertising Brochure).
"Effect of Peritoneovenous Shunting with the LeVeen Valve on Ascites" Ansley et al., *Surgery*, Feb. 1978.

*Primary Examiner*—Robert W. Michell
*Assistant Examiner*—Thomas Wallen
*Attorney, Agent, or Firm*—Kenway & Jenney

[57] ABSTRACT

In the method of treating ascites disclosed herein, an intraperitoneal inlet tube is connected to an implanted jugular catheter through a valving unit including a pair of one-way valve units which are connected in series through a flexible intermediate chamber to another pair of one-way valve units. The flexible chamber is surgically secured near the surface of the patient's abdomen or chest, preferably over the sternum, so that, by manual pressure, the patient can periodically deform the conduit thereby to effect pumping of the ascites fluid.

3 Claims, 4 Drawing Figures

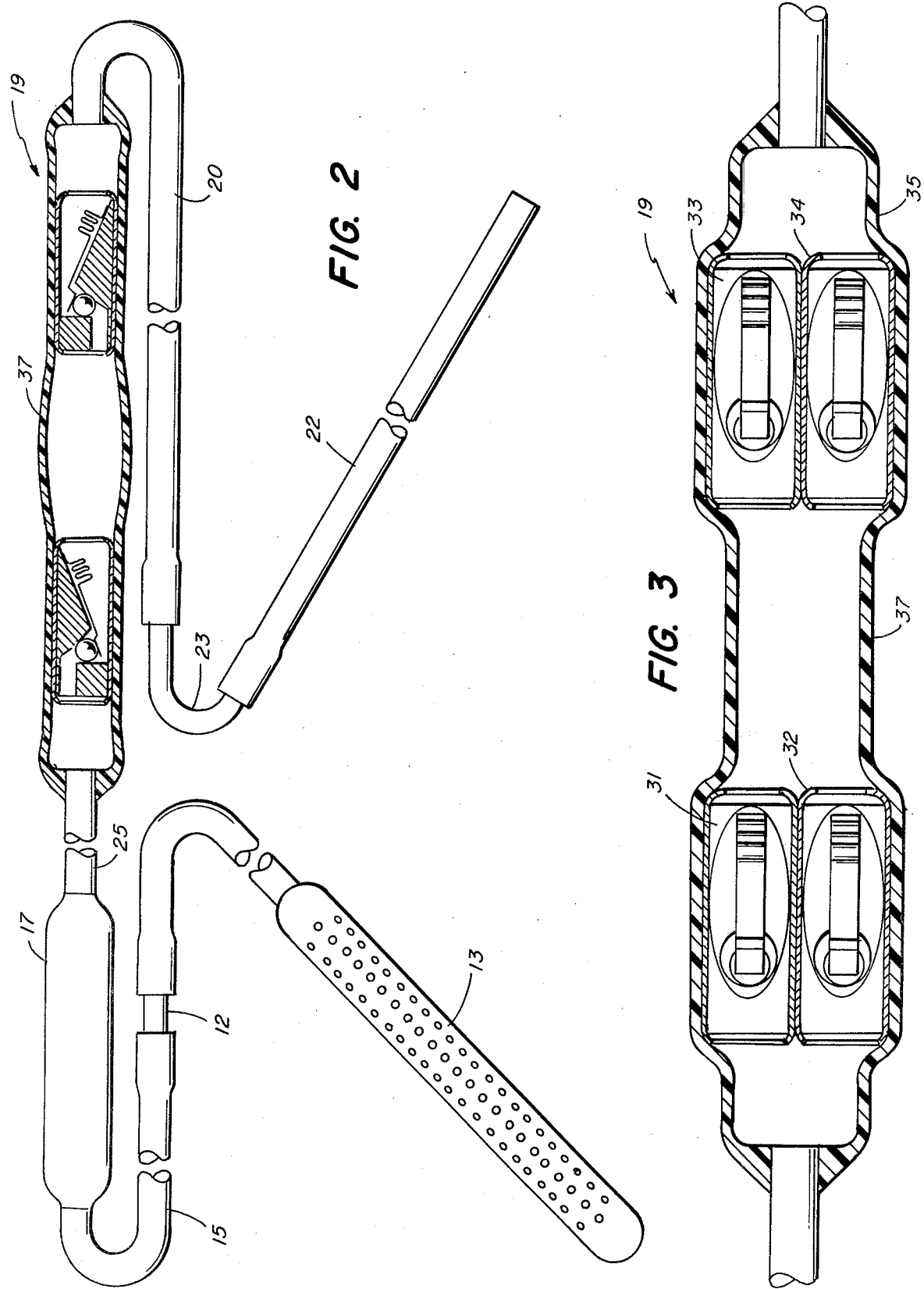

METHOD AND APPARATUS FOR THE TREATMENT OF ASCITES

BACKGROUND OF THE INVENTION

The present invention relates to the treatment of ascites and more particularly such treatment by means of an implanted peritoneo - venous shunt.

In the treatment of ascites, i.e. the accumulation of large amounts of fluid in the peritoneal cavity of the patient, it has previously been proposed to shunt or reroute ascitic fluid from the peritoneal cavity into the superior vena cava, the thoracic duct or the bladder. The providing of a shunt from the peritoneal cavity to the central venous system has offered many advantages over other types of treatment but certain difficulties have existed with prior devices and methods for effecting such treatment. The shunt devices proposed heretofore for such treatment have typically been either quite bulky, i.e. so as to require a more elaborate surgical procedure, or have been unduly subject to clogging by the presence of complex protein compounds in the ascitic fluid.

Among the several objects of the present invention may be noted the provision of an improved peritoneovenous shunt which is highly resistant to clogging; which is highly effective in the treatment of ascites; which is relatively easily implanted in a comparatively simple surgical procedure; which is of relatively simple and inexpensive construction and which is highly reliable which can be sterilized by autoclave without altering its internal mechanism. Other objects and features will be in part apparent and in part pointed out hereinafter.

BRIEF DESCRIPTION OF THE DRAWING

The invention disclosed herein will be understood better with reference to the following drawing in which:

FIG. 2 is a view, partially in section, of the overall shunt system disclosed herein;

FIG. 3 is a plan view of the valve unit of this invention; and

DESCRIPTION OF THE PREFERRED EMBODIMENT

Figure 1:
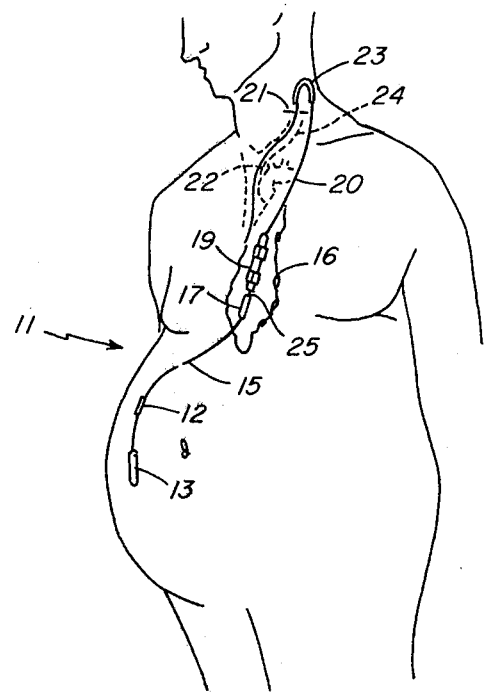
FIG. 1 is diagrammatic representation of a man with a distended abdomen.

Referring now to FIG. 1 a patient, assumed to be suffering from ascites, is indicated generally by reference character 11. In accordance with the practice of the present invention a perforate inlet catheter 13 (peritoneal catheter) is surgically introduced into the peritoneal cavity of the patient, through an abdominal incision 14, so as to provide a means for drawing off accumulated ascitic fluid. Peritoneal catheter 13 is connected by means of a straight connector 12, and a proximal tube 15 to an antechamber 17 and valve unit 19 described in greater detail hereinafter, which is implanted in a subcutaneous pocket surgically formed over the patient's sternum 16. Proximal tube 15, antechamber 17, and the valve unit 19 are implanted through a subcutaneous tunnel in accordance with conventional surgical procedures. After passing through valve unit 19, the ascitic fluid is directed into the central venous system through the distal tube 20 and atrial catheter 22. In contrast with more conventional systems, the distal tube 20 and atrial catheter 22 are of relatively small diameter. This small diameter facilitates a simpler mode of implantation wherein the distal tube is led, through a subcutaneous tunnel up to the patient's neck where a small cervical incision is made 21. Working through this incision 21, the atrial catheter 22 is inserted into the exterior jugular vein as indicated at 24. The length of the atrial catheter 22 is such to allow its tip to extend, from the point of introduction at the external jugular vein, down the superior vena cava into the patient's right atrium. After this placement, the atrial catheter 22 and the distal tube 20 are trimmed at the cervical incision and connected by the U-shape connector 23. The introduction of the atrial catheter into the external jugular vein is again made possible owing to the relatively small diameter of the catheter. Leaving the tip of the catheter within the right atrium inhibits ingrowth and eventual blockage of the catheter such as would occur if it were terminated near the point at which it enters the venous system. The overall arrangement of the shunt system is illustrated in FIG. 2 in greater detail and the actual construction of the valve unit 19 is illustrated in FIG. 3.

In accordance with the concepts of the present invention, the valving unit 19 comprises two pairs of one-way valves which are connected in series through a flexible conduit. In the preferred embodiment illustrated, four identical one-way valve elements 31-34 are employed in a series-parallel arrangement in a flexible silicone rubber housing 35 i.e. valve element 31 is in parallel with valve element 32 and this parallel pair is in series with a second parallel pair of elements 33 and 34. The series connection is established by an elongate section 37 of the silastic rubber valve housing 35. This section 37 functions as a deformable conduit for purposes explained hereinafter.

Figure 4:
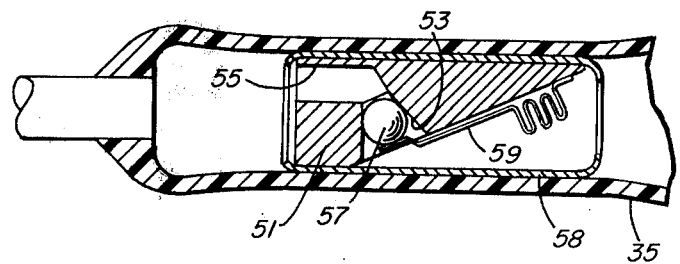
FIG. 4 is a side elevational sectional view of a valve employed in this invention.

Each of the valve elements 31-34 is generally of the type disclosed in U.S. Pat. No. 3,288,142. This construction, illustrated in FIG. 4, employs a rigid base 51 in which is formed a conical valve seat 53 connected to an inlet port 55. A rigid spherical valving element 57 is biased into the conical seat by a convoluted cantilever spring 59 which is secured to the base 51, e.g. by spot welding. A cylindrical shell 58 encloses the base 51, valving element 57 and spring 59 so as to facilitate its being held within the overall valve assembly body 35. Another suitable form of valve element is that shown in copending application Ser. No. 002,354. In each case, the one way valving is accomplished by a rigid or hard valving element (biased against a rigid seat). This is preferred over soft valving elements e.g. such as those formed of silastic rubber, in that the hard surfaces are better suited for making a seal, even in the presence of protein materials which might come to rest at the valving surface. If complete closing is not obtained some highly undesirable back flushing from the venous system may occur.

In addition to providing a larger total flow path the paralleling of valving elements is a greater protection against clogging since, even if one valving element should clog, its parallel counterpart will typically be adequate to pass a beneficial quantity of the ascitic fluid.

As noted previously, the valve assembly 19 is preferably secured e.g. in a suitable subcutaneous pocket, at a point over the patient's sternum. With the valving element assembly 19 so located, it is possible for the patient himself or his physician to effect the actual pumping of fluid from the peritoneal cavity to the central venous system by manually pressing against the valve assembly and thereby periodically collapsing or compressing the flexible conduit portion 37 between the two pairs of paralleled valving elements. As will be understood, compressing this section will expell fluid through a downstream valving element, i.e., into the venous system, while releasing the manual pressure and allowing the conduit to assume its normal shape will draw fluid into the valving unit through the upstream valves i.e. the valving elements nearest the inlet tube in the peritoneal cavity. The availability of this pumping procedure not only frees the patient from the tiresome exercies otherwise involved in generating a negative pressure within the chest and a positive pressure in the peritoneal cavity. The valving elements and the samll bore jugular catheter also can be effectively flushed by the pumping actions so that protein depostis which might otherwise tend to clog the system can be effectively cleared. In prior art systems where no such pumping action is available, it has been necessary to employ relatively large bore tubing for the venous catheter. This larger size cannot be routed up to the external jugular as can the present system nor can it be then allowed to extend along the jugular internally to a location of such that the atrium where the danger of tissuing growth is essentially absent. As indicated previously, it is highly advantageous to have the catheter enter the external jugular since it is much easier to accomplish insertion of the catheter at this point on the patient's neck where this large vein is close to the surface. This easier access often means that the procedure can be performed under a local anesthesia rather than requiring the application of general anesthesia to a patient who may already be considerably weakened by this illness.

The antechamber 17, being similarly accessible near the surface of the patient, provide a means for momentarily back flushing the peritoneal catheter 13. This is accomplished by just fully compressing the conduit portion 25 thereby effectively blocking flow through the valving elements and then compressing the antechamber itself so as to generate a momentary backflow. The antechamber also provides a convenient means for drawing off samples of ascitic fluid for analysis. For this purpose the antechamber is constructed of a flexible silicone rubber which tends to be self sealing with regard to needle punctures. The bottom of the antechamber has a metal needle stopper.

The fact that this system can be separated into its different components i.e.: peritoneal catheter 13, distal tube 20, valve unit 19, atrial catheter 22, and connectors 12 and 23; makes any surgical revision simple since there is no need to remove the whole system, but only the failing part. By proper use of the antechamber and the valve pumping chamber, a failure along the system can be easily located.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. A method for the treatment of a patient suffering from ascites comprising:
    implanting an inlet catheter in the peritoneal cavity of the patient;
    inserting, into the patient's jugular vein, a drainage catheter which extends essentially to the right atrium;
    connecting said inlet catheter to said drainage catheter through a valve assembly comprising a first pair of one-way valves in side by side relationship connected in series through a flexible conduit to a second pair of one-way valves in side by side relationship
    surgically securing the valve assembly near the surface of the patient's abdomen so that, by manual pressure, the patient can deform said conduit to effect pumping of ascitic fluid from the peritoneal cavity to the venous system.

2. A method for the treatment of a patient suffering from ascites comprising:
    implanting an inlet catheter into the peritoneal cavity of the patient;
    inserting, into the patient's central venous system, a drainage catheter;
    connecting said inlet catheter to said drainage catheter through a valve assembly comprising a first pair of one-way valves in side by side relationship connected in series through a flexible conduit to a second pair of one-way valves in side by side relationship
    surgically implanting the valve assembly in a subcutaneous pocket over the patient's sternum so that, by manual pressure, the conduit can be deformed to effect pumping of ascitic fluid from the peritoneal cavity to the venous system.

3. The method as set forth in claim 1 further comprising inserting an antechamber between said inlet catheter and said valve assembly.

* * * * *